United States Patent [19]

Meyer et al.

[11] 4,109,314
[45] Aug. 22, 1978

[54] AUTOMATIC FRUIT ANALYZER

[75] Inventors: Stephen F. Meyer, Columbus; Amiel R. Helle, Westerville; Leo J. Niese, Toledo, all of Ohio

[73] Assignee: Reliance Electric Company, Cleveland, Ohio

[21] Appl. No.: 748,850

[22] Filed: Dec. 8, 1976

[51] Int. Cl.[2] .................... G06F 15/46; G01N 33/02
[52] U.S. Cl. ............................ 364/552; 23/253 R; 73/61.1 R; 364/567
[58] Field of Search .................... 235/151.12, 151.3; 23/253 R; 73/61 R, 61.1 R, 437, 451; 364/552, 551, 556

[56] References Cited

U.S. PATENT DOCUMENTS

| | | | |
|---|---|---|---|
| 3,625,655 | 12/1971 | Culp et al. ........................ | 23/253 R |
| 3,728,080 | 4/1973 | Moran ............................. | 235/151.12 |
| 3,769,178 | 10/1973 | Rothermel, Jr. .................. | 23/253 R |
| 3,777,127 | 12/1973 | Goetchius et al. ............... | 73/61.1 R |
| 3,880,589 | 4/1975 | Jones .............................. | 23/253 R |
| 3,893,333 | 7/1975 | Sunahara et al. ................ | 73/61 R |

*Primary Examiner*—Felix D. Gruber
*Attorney, Agent, or Firm*—Ronald B. Brietkrenz

[57] ABSTRACT

A fruit analyzer for testing fruit and fruit juice samples to automatically obtain test data relating thereto and for using the test data so obtained to compute and print out characteristic parameters indicating the nature and quality of the fruit tested, including per cent acid and soluble solids content. A computer controlled testing unit has a suspended plummet soluble solids testing means including plummet weight and temperature transducers as well as an acid testing means including liquid weight and PH transducers for automatic titration of the contents thereof. A network of valved conduits deliver and drain juice, rinse solution, and cleaning solution at the appropriate time into and from the soluble solids and acid testing means. A separate network of valved conduits is provided to deliver alkali at the appropriate time to the acid testing means. The computer is caused by an operating sequence to read the weight of the plummet in air, load juice samples into the soluble solids testing means and the acid testing means, read the juice temperature and weight of the plummet in the sample juice in the soluble solids testing means, and then read the weight of juice in the acid testing means, titrate the juice in the acid testing means to a selected PH level, read the weight of the titrated juice and then compute the desired characteristic parameters indicating the nature and quality of the samples tested. The desired characteristic parameters are then printed and the testing unit is caused to go through a rinsing cycle.

2 Claims, 9 Drawing Figures

END OF BRIX-ACID TEST ROUTINE

AUTOMATIC FRUIT ANALYZER

BACKGROUND OF THE INVENTION

This invention relates generally to automatic measuring and testing apparatus and more particularly to an apparatus for testing fruit and fruit juice and for computing a variety of characteristic parameters which are accepted in the citrus fruit industry as indicating the nature and quality of the fruit or fruit juice.

In the fruit growing industry and particularly in the citrus fruit growing industry, fruit is harvested from the groves and transported to terminals or processing plants for sale. The selling price of the fruit crop is largely determined by the nature and quality of the fruit.

Conventionally, the fruit quality is determined by a variety of laboratory like tests which are manually performed away from controlled laboratory conditions. These tests include the determination of the soluble solids content, commonly measured in degrees Brix, and the acid content of the juice, commonly measured as a per cent acid. The results of these tests are used in computations to determine characteristic parameters of the sample fruit, which characteristic parameters include the ratio of soluble solids content to acid content, the weight of juice in a standard box of fruit, and the weight of soluble solids in a standard box of fruit.

These tests are conventionally manually performed and the results thereof depend to a large degree upon the eyesight and judgement of the inspector performing the tests. In addition, there is great opportunity for introducing error in this type of arrangement due to the manual transferring the test data to the computational stage, the opportunity for incorrectly performing the computations, or the possibility of attributing the results of a particular computation to the wrong fruit sample. As a result, this testing process has heretofore been a long and tedious operation whose results were not highly reliable.

There is, therefore, a need for a means which is capable of performing these tests which requires a minimum of operator interaction, performs the tests and does the necessary calculations in a minimum amount of time, and reduces errors.

The present invention solves this need by providing an automatic fruit analyzer which automatically performs the required tests and calculates the desired parameters with a minimum of operator interaction, in a minimum amount of time, and to a high degree of accuracy.

Apparatus for determining the specific gravity of a liquid is well known in the art and includes the devices disclosed in Gipe et al, U.S. Pat. No. 1,205,986, Burningham et al, U.S. Pat. No. Re. 17,728, Wallace, U.S. Pat. No. 3,071,971, Weichselbaum et al, U.S. Pat. No. 3,332,289 and Fann, U.S. Pat. No. 3,821,901. Similarly, apparatus for automatically titrating liquids is known and includes the devices shiwn in Prohaska, U.S. Pat. No. 3,730,685, and Rellstab et al, U.S. Pat. No. 3,870,466.

Although the use of a float type arrangement for use in the determination of the specific gravity of a liquid is known in the art, none of the cited references discloses a float type arrangement in conjunction with a load cell transducer yielding an analog output proportional to the forces exerted on the float type arrangement. Additionally, none of the cited references provides a means whereby errors introduced into the measurement process by a change in weight of the float type arrangement, for example caused by a build-up of deposits thereon, may be eliminated. Even further, none of the references discloses a means for eliminating the errors introduced into the specific gravity measurement by the temperature of the liquid being measured.

None of the above cited references relating to apparatus for automatic titration discloses an automatic means for titrating by weight. Titration by weight allows a much simpler and more economical apparatus to be used for the titration process since very accurate volumetric measurements are not required to perform the titration process.

In general, previous attempts to mechanize acid content or soluble solids content testing equipment, particularly those using refractometers, have attempted to control and standardize all of the conditions of the test sample. For example, they attempted to maintain the juice at an exact temperature and precisely control the flow rate of juice during the test. Consequently, variations in the conditions of the test sample caused variations in the accuracy of the test data. The difficulties in controlling the conditions of the test sample made automation of the test procedure effectively impossible due to the large number of highly variable factors involved. The present invention eliminates this problem by correcting for changes in the test sample.

SUMMARY OF THE INVENTION

The present invention is directed to a fruit analyzer for testing a sample of fruit juice supplied from a juice supply container. The analyzer has a soluble solids content testing means for use in determining the soluble solids content of the juice. The soluble solids content testing means includes a first vessel for receipt of a fruit juice sample, a plummet suspended into the first vessel from a first weight transducer and a temperature transducer for detecting the temperature of the first sample of fruit juice contained in said first vessel. The analyzer also has an acid testing means for use in determining the acid content of the fruit juice sample. The acid testing means includes a second vessel for receipt of a juice sample, which second vessel is supported by a second weight transducer. A PH transducer is mounted within said second vessel to detect the PH of the second sample of fruit juice and a stirrer is also provided for mixing the contents of the second vessel. An alkali source is connected through an electrically operable alkali inlet valve to deliver alkali to the second vessel for automatic titration of the contents thereof. A network of valved conduits conveys the fluid upon appropriate commands from an assoiocated computer. This network includes a pair of valved inlet conduits from the juice supply container, one connected to the first soluble solids test vessel and the other connected to the second acid test vessel. A computer for controlling the testing unit and for computing and storing data is operatively connected to the valves of the conduit network, the transducers and to the stirring means. The computer records in response to instructions from the operating sequence, data representing the weight of the plummet suspended in the first vessel when it is empty, loads a sample of juice through the inlet conduits into the soluble solids content testing vessel and the acid content testing vessel, and records data representing the temperature of the sample of juice in the soluble solids content testing vessel, the weight of the plummet in the sample of juice in the soluble solids content vessel and the weight of the juice sample in the acid content testing vessel. The computer then activates the stirrer, opens the alkali inlet valve and delivers alkali into the second juice sample in the acid content test vessel to titrate the second sample to a selected PH. The computer then records data representing the weight of the titrated juice sample in the acid content vessel and computes the acid and soluble solids content of the juice. Various other parameters are also computed.

Accordingly, it is one of the objects of the present invention to provide an automatic fruit analyzer which automatically tests fruit and fruit juice and provides a printed output of the characteristic parameters of the fruit, which analyzer makes no attempt to control or modify the test environment factors, but rather measures the existing test environment factors in computing the tests results.

Further objects and features of the invention will be apparent from the following specification and claims when considered in connection with the accompanying drawings illustrating an exemplary embodiment of the invention.

In describing the exemplary embodiment of the invention, which is illustrated in the drawings, specific terminology will be resorted to for the sake of clarity, however, it is not intended to be limited to the specific terms so selected, and it is to be understood that each specific term includes all technical equivalents which operate in a similar manner to accomplish a similar purpose.

DETAILED DESCRIPTION

Figure 1:
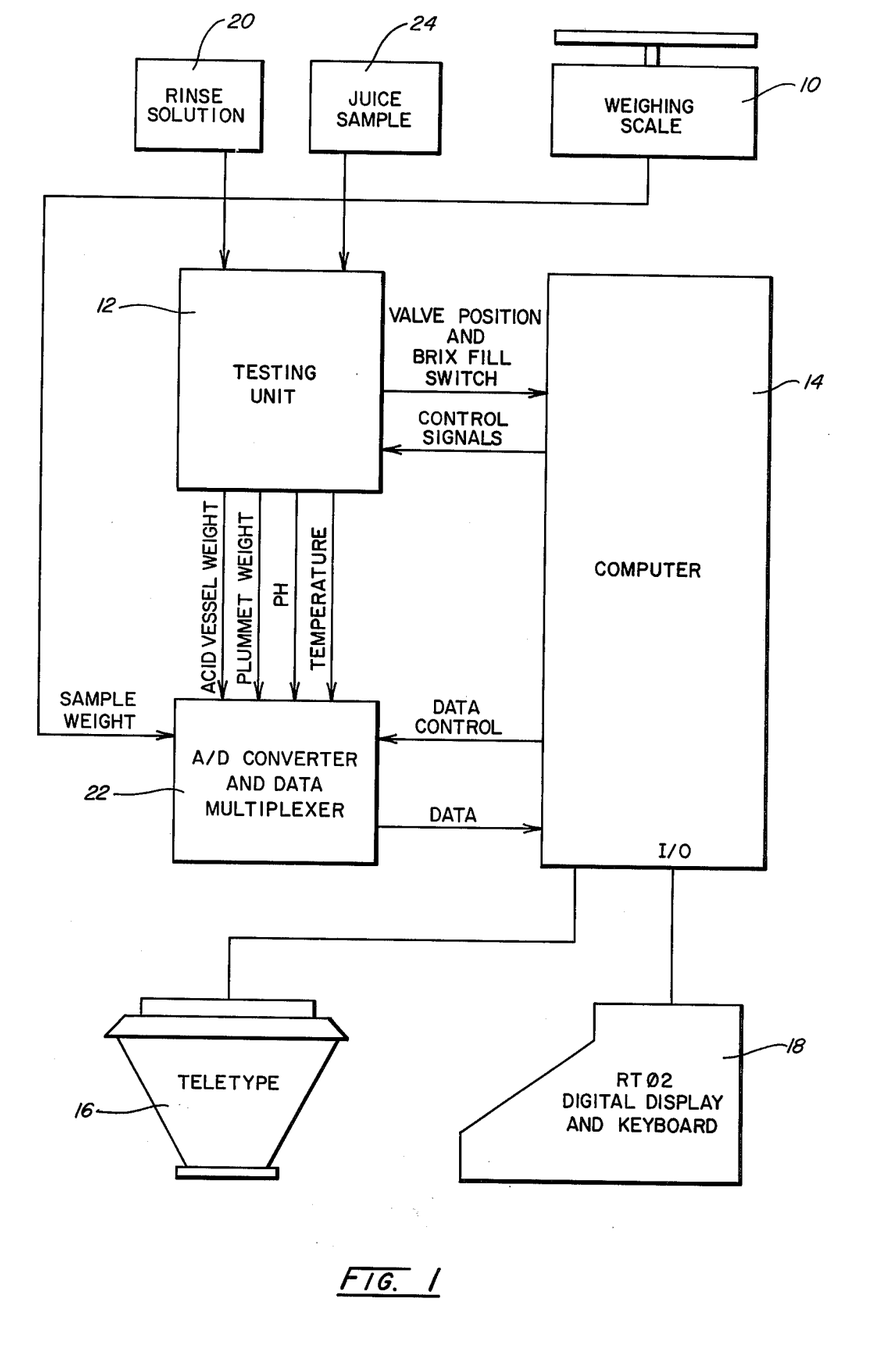
FIG. 1 is a block diagram illustrating an exemplary embodiment of the invention.

FIG. 1 is a block diagram illustrating a system embodying the present invention. The system has a weighing scale 10, which may be a Model 2084 scale manufactured by Toledo Scale, Division of Reliance Electric Company for weighing fruit and fruit juice samples. The scale 10 provides an electrical analog singla proportional to the weight on its platter to the A/D converter and data multiplexer 22, which converter-multiplexer 22 provides a digital output corresponding to the analog signal provided by the scale 10 to the computer 14. The computer 14 is used for controlling the testing unit 12 and for inputting data from the scale 10, the digital display and keyboard 18 and the A/D converter and data multiplexer 22. The computer 14 may be a Model PDP-11 computer manufactured by Digital Equipment Corp. In addition, the computer 14 computes parameters from the input provided by the converter-multiplexer 22 and the display keyboard 18 and causes these parameters, indicative of the nature and quality of a juice sample, to be outputted on the teletype 16. The teletype 16 may be a type ASR-33 teletype and the digital display keyboard 18 is preferably a model RTO2 display and keyboard manufactured by Digital Equipment Corporation, Maynard, Massachusetts.

Testing unit 12 is used for subjecting a fruit juice sample to a series of tests in order to obtain data for use in determining the soluble solids content and the acid content of the juice sample. The testing unit 12 has a plurality of conduits and valves (shown in detail in FIG. 3) for causing fruit juice to be transferred from a juice sample container 24 to a plurality of test vessels mounted within the testing unit 12 and for subsequently causing the fruit juice to be transferred from the test vessels to a waste disposal (not shown). The testing unit 12 also includes a plurality of transducers for measuring a variety of test conditions and variables during the testing procedure and for supplying the data from these transducers to the computer 14. The transducers are intermediately connected to the A/D converted and data multiplexer 22.

Figure 2:
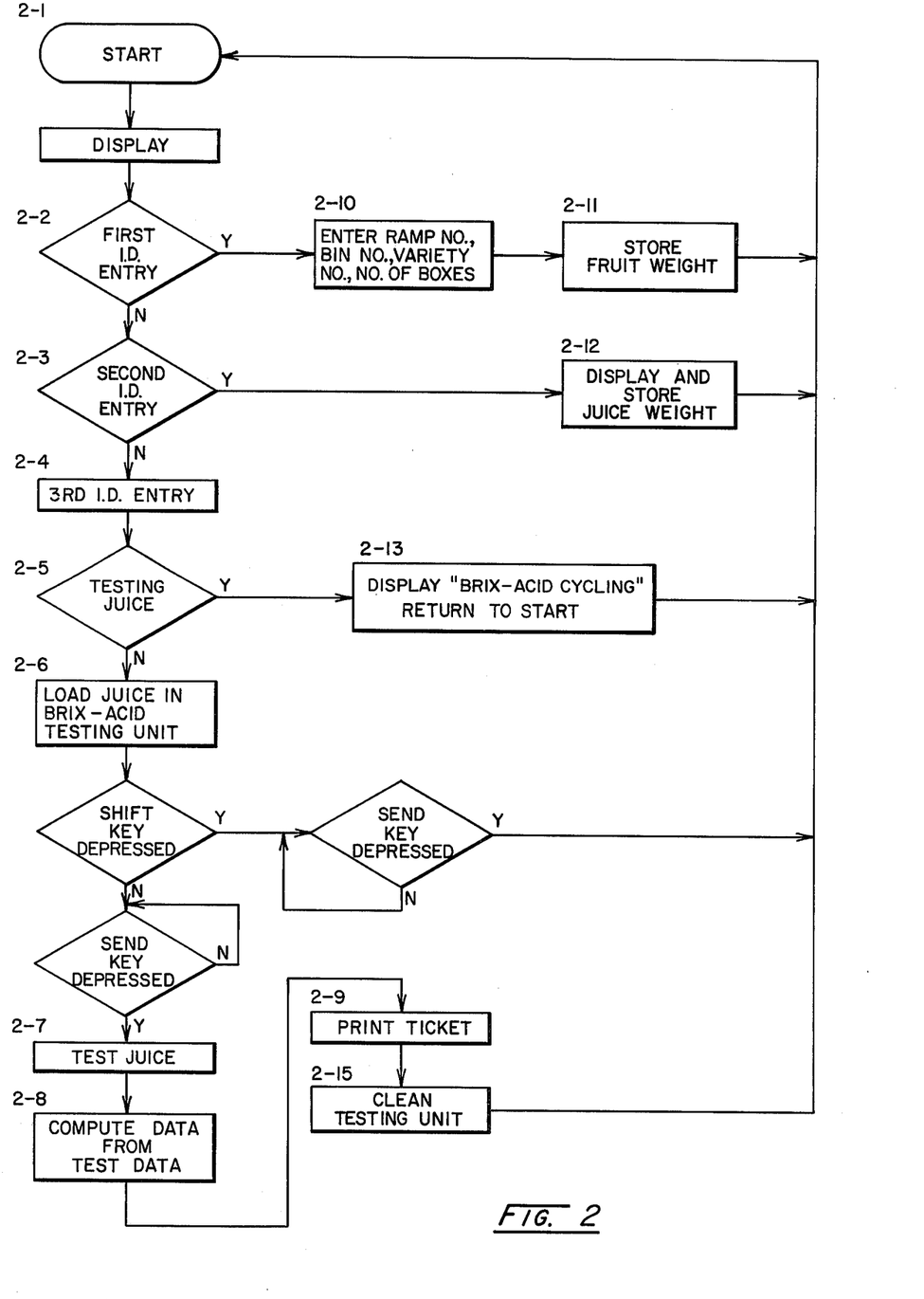
FIG. 2 is a flow diagram indicating the operation of the embodiment of the invention which is illustrated in FIG. 1.

FIG. 2 is a flow chart illustrating in a general and simplified manner the operation of the embodiment of the invention which is illustrated in FIG. 1. Operation is discussed with reference to computer 14 for which a suitable program has been prepared. The subsequent flow charts and detailed description of the operation of the entire system will enable a person of ordinary skill in the computer programming art to develop a suitable program. However, the actual program used to implement the exemplary embodiment of the present invention is included as an appendix to the specification.

The operator begins testing a fruit crop by placing a selected sample of whole fruit in a suitable container and placing the container of fruit on the weighing scale 10. The weight is continuously displayed on the RTO2 terminal 18.

Operation of the system is initiated at step 2-1 by the operator depressing the send key, or other appropriate key which may be chosen by the computer programmer as the incrementing key, on the keyboard of the RTO2 terminal 18. The operating sequence, as described below, then causes a display of the words "Enter ID No" on the terminal 18. The operator then enters on the RTO2 terminal 18, as indicated by step 2-2, an identification number associated with the particular fruit sample and again depresses the send key to continue in the operating sequence. For reasons which will subsequently appear, the computer then scans its memory to determine whether a fruit weight has been stored in association with this identification number. If a fruit weight associated with the particular identification number has not been entered, the operations indicated by step 2-10 of FIG. 2 are then performed by the operator.

In step 2-10 the program sequence calls, via the display on the RTO2 terminal 18, for the ramp number which the operator enters on the RTO2 terminal 18 and then causes the operating sequence to continue by depressing the send key. In turn, the bin number, variety number and number of boxes all associated with the particular sample are then called for by the computer and provided by the operator in a manner similar to the ramp number. After the number of boxes is entered and the operating sequence is again caused to continue by depressing the send key, the computer stores the weight of the fruit sample in memory in association with the sample's identification number and returns to start, at step 2-1.

The operator may then weigh other fruit samples and store the appropriate data associated therewith in the manner described above. In addition, the operator may at any time use a conventional juice extractor to extract the juice from a previously weighed sample of fruit. The extracted juice may then be weighed by placing it on the weighing scale 10, whereupon the computer 14 via terminal 18 again asks for the ID number associated with the sample of fruit from which the juice was extracted. After the entry of the associated identification number (ID), the computer interrogates its memory to determine whether this is the first time this ID has been entered, indicating whether a fruit weight has been entered in asscoiation with this ID. If a fruit weight has not been entered in association with this ID, the computer would consider this weight to be a fruit sample weight and would progress through steps 2-10 and 2-11. If, however, the computer does find that this ID was previously entered and hence that there is a fruit weight in its memory associated with this particular ID, the computer interrogates its memory to determine whether this is the second time that this ID has been entered, indicating whether juice weight data has been entered for that ID number. Upon finding that this is not the second time this ID has been entered and hence that no juice weight data has been entered, the scale weight is entered into memory as the juice weight associated with that ID number. The system is then returned to start at step 2-1 via step 2-12.

The operator may then similarly weigh other fruit and fruit juice samples and store the appropriate data associated therewith. At the same time a previously weighed juice sample may be deaerated by conventional deaeration equipment and loaded into a juice sample container 24 (FIGS. 1 and 3) connected to the testing unit 12. Having loaded a juice sample, the operator may again depress the send key and cause the operating sequence to request the ID number. Upon entry of the ID number, the computer scans its memory and upon determining that fruit weight and juice weight data have been entered for that ID number, causes the operating sequence to go to step 2-5. At step 2-5 the computer 14 interrogates the testing unit 12 to determine whether the testing unit 12 is currently engaged in testing juice. If the testing unit 12 is engaged in testing juice, the RTO2 terminal 18 displays the words "Brix-Acid cycling, reload third ID". This returns the operating sequence to start at step 2-1, thereby allowing other fruit or juice to be weighed while the testing unit 12 completes its testing cycle.

The operator may subsequently enter the ID number associated with the loaded juice sample again determine if the testing unit 12 has completed its testing cycle. If the testing cycle is complete, the computer 14 will then display the instruction at step 2-6 to load the juice in the Brix-Acid testing unit. The operator may thereupon alternatively either return to start by depressing the shift begin key if some problem has developed or cause the operating sequence to continue by depressing the send key and thereby initiate the automatic juice test cycle. Upon initiating the automatic juice test cycle the computer 14 will then operate the valves of the testing unit 12 and load the juice sample into the testing unit 12 and begin testing the juice. When the juice testing cycle begins the operator may simultaneously weigh other fruit or fruit juice samples while the first juice sample is being tested.

After the testing unit 12 has completed its testing cycle and has supplied data to the computer 14, the computer computes the desired parameters from the test data, prints the resulting data on a ticket and initiates the rinsing of the testing unit 12.

Because the system of the present invention always identifies each sample with an appropriate identification number and because the system maintains a record of the data entered in association with each sample, the operator is not required to completely test each sample before beginning the testing of another sample. Instead, the operator may weigh whole fruit, or juice and may test juice for soluble solids and acid content simultaneously.

Figure 3:
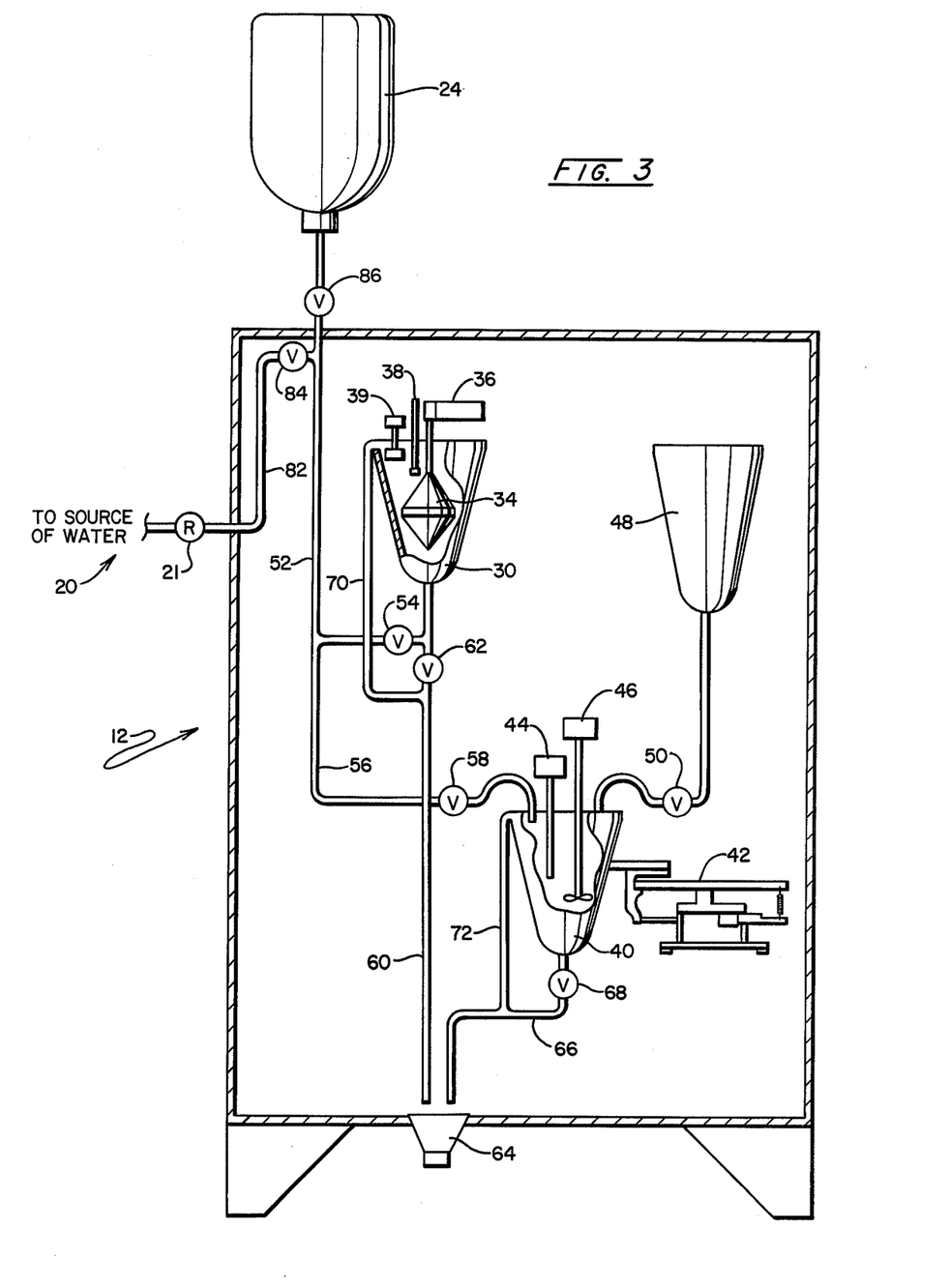
FIG. 3 is a schematic diagram illustrating the Brix-Acid testing unit of the embodiment of the invention illustrated in FIG. 1.

FIG. 3 illustrates in detail the structure of the testing unit 12 schematically illustrated in FIG. 1. The purpose of the testing unit 12 is to provide data to the computer 14 for computing the soluble solids content of the juice in degrees Brix and for determining the per cent by weight of acid in the juice sample. The test unit 12 comprises a soluble solids testing means for use in determining the soluble solids content of the juice, an acid testing means for use in determining the acid content of the juice and a network of valved fluid conveying conduits for supplying juice and subsequently supplying rinse solution to these testing means and for draining juice and rinse solution from these testing means.

Referring now to FIG. 3, the testing means 12 has a first soluble solids test vessel 30 for receipt of juice from the juice sample container 24. A plummet 34, of biconical shape, is suspended into this test vessel 30 from a first weight transducer 36 such that when the soluble solids test vessel 30 is completely filled with juice, the biconical plummet 34 is completely immersed in the juice. Preferably the weight transducer 36 is a load cell providing an electrical analog output signal proportional to the force exerted by the plummet on the transducer 36.

A temperature transducer 38, preferably of the thermocouple type, is mounted to extend into the Brix test vessel 30 for immersion in its contents so that it can detect the temperature of the juice in the soluble solids test vessel 30. In the exemplary embodiment, the temperature transducer 38 is the transducer of a Model 9300 digital temperature indicator manufactured by Electronic Research Co. The soluble solids test vessel 30 is also provided with a float switch 39 for indicating that the vessel 30 is filled.

The acid testing means includes a second, acid test vessel 40 for receipt of juice from the juice sample container 24. The acid test vessel 40 is supported by a second weight transducer 42 for providing an electrical analog output signal which is proportional to the sum of the forces exerted by the liquid in the acid test vessel 40 and the acid test vessel 40. Preferably this second weight transducer 42 is a cantilevered beam scale having a load cell associated therewith.

The acid testing means, under control of computer 14, automatically performs a titration of the juice which is loaded into the acid vessel 40. A conventional stirrer 46 is provided to mix the contents of the acid test vessel 40 during this titration.

A PH transducer 44, which may be a transducer from a Model 601-A-PH meter manufactured by Orion Research is used for determining the degree of alkalinity or acidity of the liquid in the acid test vessel 40 and is mounted to detect the PH of the liquid in the acid test vessel 40.

In order to perform the titration, an alkali source 48 is mounted above the acid test vessel 40 and connected through an electrically operable alkali inlet valve 50 to deliver alkali into the acid test vessel 40. Preferably the alkali inlet valve 50 is capable of a full-on position, a partially-on position and an off position so that two different alkali delivery rates may be utilized in performing the titration.

The network of valved, fluid conveying conduits, which transfer fluids in the testing unit 12 under control of the computer 14, includes a sample fill conduit 52 extending from the juice supply container 24 to the test vessel 30 and having an interposed Brix test fill valve 54. The network also includes a similar fill conduit 56 extending from the conduit 52 to the acid test vessel 40 and having an interposed acid sample shut-off valve 58. It is advantageous to the present invention that the inlet conduit from the juice supply container 24 to the test vessel 30 be connected to the bottom of the test vessel 30 so that this vessel is filled from the bottom, thereby avoiding air vortexes and turbulence and consequently avoiding the introduction of air into the previously deaerated juice.

A drain conduit 60 extends from the bottom of the test vessel 30 through an interposed drain valve 62 to a waste receiver 64 for draining tested juice samples and rinse water from the soluble solids test vessel 30. Similarly, a drain conduit 66 extends from the bottom of the acid test vessel 40 through an acid test drain valve 68 to the waste receiver 64 for the same purpose.

The soluble solids test vessel 30 and the acid test vessel 40 each have overflow drains 70 and 72 respectively.

In order to automatically purge and cleanse the test vessels and equipment to prevent the build-up of deposits, a rinse solution source 20, which in the exemplary embodiment may be a source of water regulated by a pressure regulator 21, is connected to a rinse solution inlet conduit 82 which has a rinse shut-off valve 84 and is connected to supply the rinse solution to fill conduit 52 near the valve 86 outlet. At the appropriate times after testing, the computer 14 permits the draining of samples and the opening of the inlet valve 84 for the circulation of rinse solution through the vessels and the conduits.

At the end of each day of use, a container of wash solution, such as a dilute alkali, can be connected in place of the juice supply container 24. The testing routine may then be initiated to thoroughly cleanse the system and then rinse it with water in the same manner as the testing routine is performed. However, the operating sequence may be modified to eliminate the ticket printing.

As indicated in FIG. 1, the output signals of the soluble solids load cell 36, the acid vessel load cell 42, the Brix temperature transducer 38 and the PH transducer 44 are connected to the computer 14 via the A/D converter and data multiplexer 22 to indicate respectively the weight of the plummet 34, the weight of the acid test vessel 40, the temperature of the juice in the soluble solids test vessel 30 and the PH of the juice in the acid test vessel 40. Additionally, all valves, the stirrer 46, the Brix fill switch 39 and the desired indicating lamps are connected either directly or indirectly to the computer 14.

Figure 4:
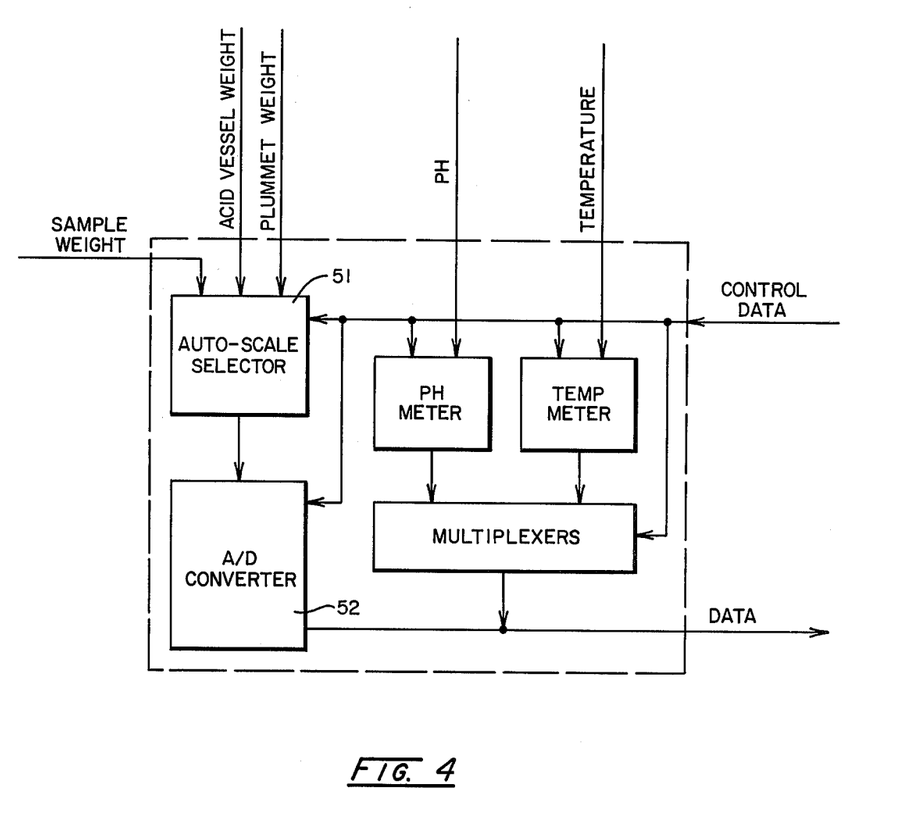
FIG. 4 is a block diagram showing details of the A/D converter and data multiplexer shown in FIG. 1.

The converter-multiplexer 22, illustrated in more detail in FIG. 4, includes a conventional multi-position, select switch 51 which determines which of the analog signals from the weighing scale 10, the plummet weight load cell 36 and the acid test vessel weight transducer 42 are inputted via the A/D converter 52 to the computer 14. The select switch 51, which may be a Toledo Auto Scale Selector, applies one of the three weight signals to an analog to digital converter 52 to provide computer readable data. The analog to digital converter 52 is preferably a Model 8130 digital indicator manufactured by the Toledo Scale Division of Reliance Electric Company. Since three analog weight signals are applied to the select switch, three of its positions are used and these are identified in FIGS. 5A–E as ASS-1 for the weigh scale 10, ASS-2 for the plummet weight load cell 36 and ASS-3 for the acid test vessel load cell 42.

FIGS. 5A–E of the drawings illustrate and describe the operating sequence of the exemplary embodiment of the invention which is illustrated in FIGS. 1–4. FIGS. 5A–E are in flow chart form and may be used by those skilled in the computer programming art to program a general purpose digital computer so that it may operate as a part of the examplary embodiment of the invention.

Figure 5A:
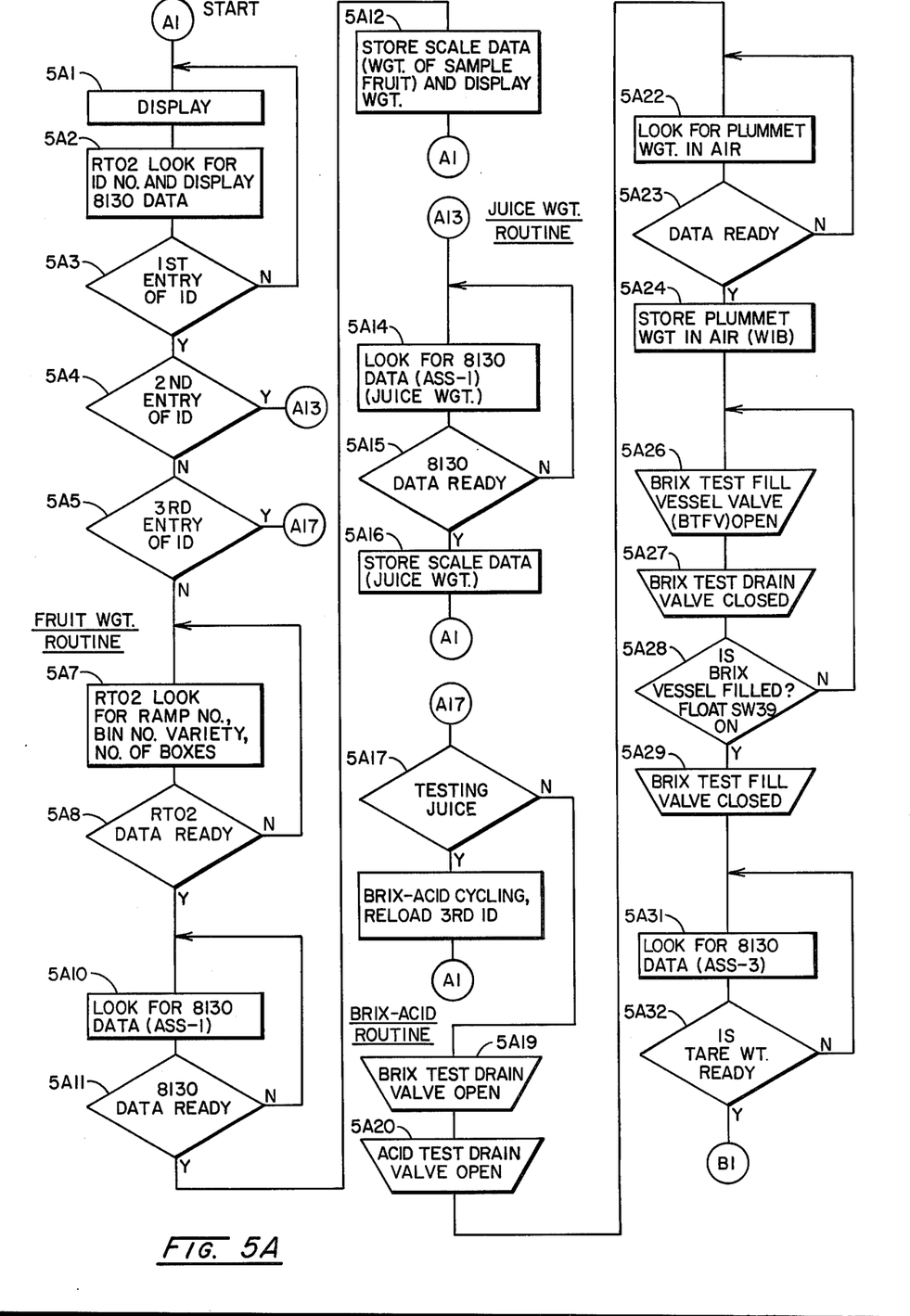
FIGS. 5A–E are flow diagrams illustrating the details of the operating sequence of the preferred embodiment of the invention.

Referring now to FIG. 5A of the drawings for a more detailed description of the operating sequence of the examplary embodiment, there is shown that under initial conditions the computer has switched the select switch 51 to its first position so that the weight of objects on the weighing scale 10 is continuously displayed on the digital display readout of the RTO2 terminal 18 as indicated by step 5A1. The system will continue in this state until the send key is depressed so that an operator may weigh whatever he wishes without initiating the remainder of the sequence.

However, the remainder of the sequence may be initiated by depressing the send key and thereby causing the sequence to display a request for an ID number on the RTO2 terminal 18. Upon entry of the appropriate ID number computer scans its appropriate memory to determine whether this is the first, second, or third entry of that particular ID number denoting that no data, fruit weight data or fruit weight data and juice weight data respectively have been entered in association with that particular ID number as shown in steps 5A2-5A5. If there is fruit weight data but no juice weight data for that ID number, the program branches to A13 to initiate a juice weighing routine. If there is both fruit weight data and juice weight data associated with that ID number, the program branches to A17 to initiate the Brix-Acid routine.

Assuming that a sample of whole fruit is initially positioned on the weighing scale 10, then there should be no previous fruit weight data associated with this sample in the computer memory. After the operator depresses the send key, enters the appropriate ID and again depresses the send key the program sequence begins the fruit weighing routine beginning at 5A7 by requesting the ramp number. Upon its entry by the operator, the computer requests a bin number, upon its entry requests the variety and upon its entry requests the number of boxes.

After this data has been entered by the operator, the computer will look for the weighing scale 10 data at the output of the 8130 analog to digital converter as indicated by step 5A10. Upon receipt of the weighing scale 10 data, which represents the weight of the fruit, the computer stores this weight in memory in association with its ID number. The fruit weighing routine is then ended and the sequence loops back to A1.

With the return to A1, the RTO2 display will again display whatever weight is placed upon the weighing scale 10. However, upon depression of the send key to advance the sequence, the computer again requests an ID number. Upon entry of an ID number, the computer again scans to determine whether a fruit weight has been stored in association with that ID number. If the identification number is being entered for the second time, fruit weight data will be stored in the computer memory but there will be no juice weight data so the program will branch to the juice weighing routine at A13.

Assuming now that the juice has been extracted from the above noted sample of whole fruit and deaerated and placed on the scale 10, the computer will look, after entering the appropriate ID as indicated above, for weight data from the weighing scale 10 and upon receipt of this data will store this weight as the juice weight associated with the associated sample identification number. The juice weighing routine is ended and the sequence loops back to A1.

The operator may again position either fruit or juice upon the weighing scale 10 and perform the above fruit weighing or juice weighing sequence. Alternatively, if the previously weighed deaerated juice sample has been placed in the juice sample container 24, the juice sample container 24 may be connected to the juice sample inlet 86 in preparation for the Brix-Acid testing procedure. The operator then depresses the send key to increment the program. The RTO2 terminal 18 will again display a request for the identification number. Upon entry of the identification number, the computer again scans its memory and if it finds that fruit weight data and juice weight data has been stored in association with the identification number, as is the case for the assumed example, the program will branch to the Brix-Acid testing routing beginning at A17.

If a juice testing procedure is in operation, the computer will display that information and an instruction to the operator to reload the third ID and then will cause the operating sequence to loop back to A1. In that case, the third entry of the identification number must be repeated as described above at a subsequent time after the testing operation has been completed.

If the ID number is inserted for the third time at a time when the Brix-Acid testing unit is not testing, the Brix test subroutine is then begun at 5A19. The drain valves 62 and 68 for the soluble solids test vessel 30 and the acid test vessel 40 are opened to drain out rinse water left there at the conclusion of the prior testing and rinse routines. The automatic select switch 51 is switched to its second position by the computer 14 and interrogates the load cell 36 to determine the weight of the plummet 34 in air. When the plummet weight in air is available it is stored in computer memory as indicated by step 5A24.

The computer 14 then causes the Brix test fill valve 54 to be opened and closes the Brix test drain valve 62 until the float switch 39 indicates to the computer 14 that the Brix test vessel 30 has been filled. The Brix test vessel fill valve 54 is then closed.

The computer then reads and stores the weight of the empty acid sample vessel 40 at steps 5A31-5A32 for use in subsequent computations. This also allows some time for the contents of the Brix test vessel 30 to settle and stabilize.

Figure 5B:
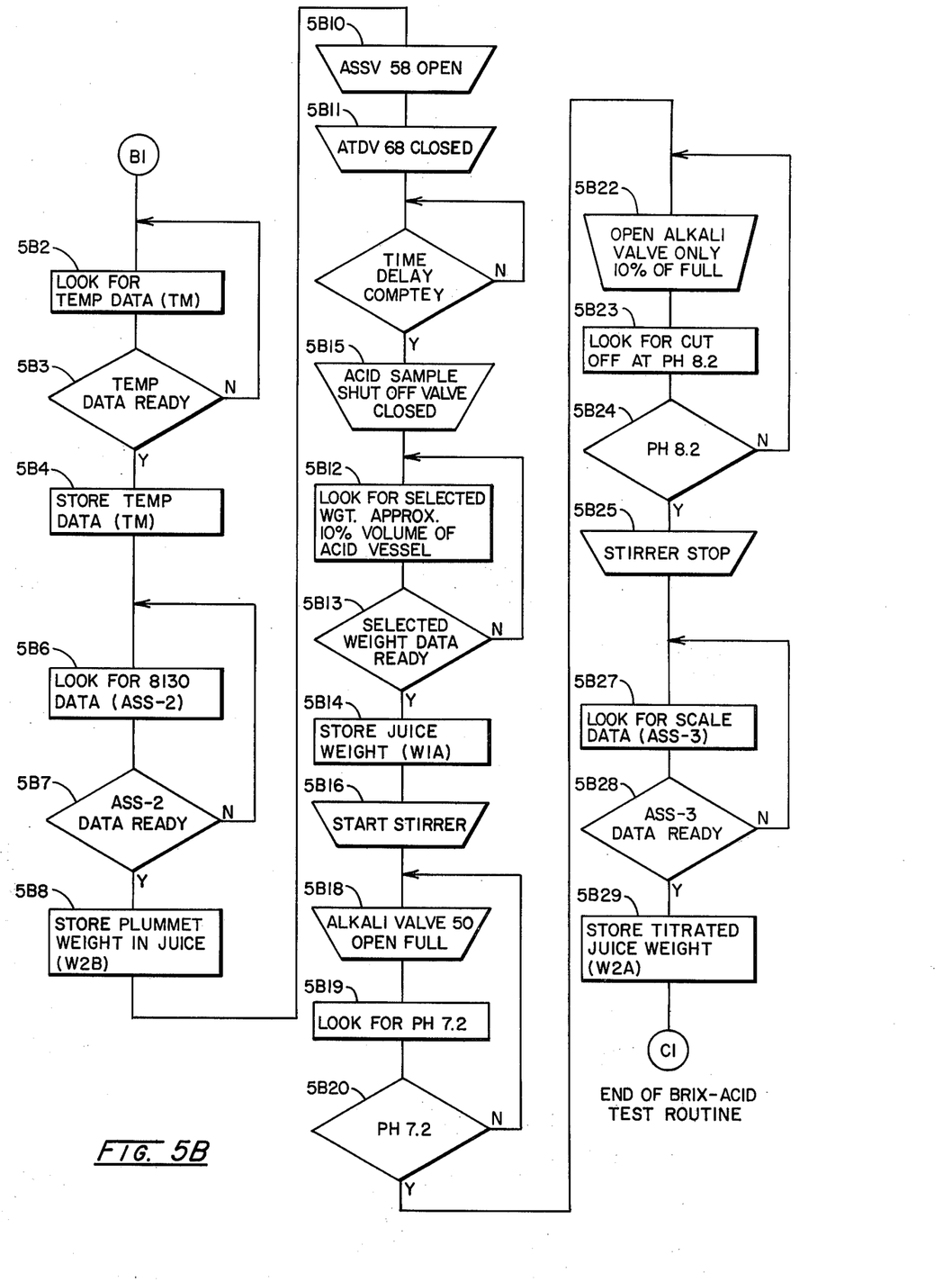

Referring now to FIG. 5B, after storing the weight of the empty acid sample vessel 40, the computer interrogates the temperature transducer 38 at step 5B2 to determine the temperature of the juice sample which has been filled into the soluble solids test vessel 30. Data representing this temperature is then stored in memory at step 5B4 and the computer again interrogates the load cell 36 and obtains and stores data representing the weight of the plummet 34 in the juice sample contained in the soluble solids test vessel 30.

At step 5B10 the computer begins the acid test subroutine by opening the acid sample shut-off valve 58 and closing the acid test drain valve 68 to admit a sample of juice from the juice sample container 24 into the acid test vessel 40.

By previous laboratory testing, the weight which is detected by the weight transducer 42 when the acid test vessel 40 is approximately 10% filled has been determined and stored in the computer. Consequently the computer may monitor the output of the weight transducer 42 and when the output of the weight transducer 42 equals this selected weight, the acid sample shut-off valve is closed and the precise weight computed. Filling the acid sample test vessel 40 to only approximately 10% of its capacity assures that it will not overflow during the automatic titration which is to follow.

The computer then starts the stirrer 46, opens the alkali shut-off valve 50 to its full open position to begin the titration step at 5B19. The computer 14 also monitors the signal from the PH transducer 44 until the PH reaches 7.2. Upon reaching a PH of 7.2 the alkali shut-off valve 50 is switched to its partially open position, which is preferably 10% of its full open position. The introduction of alkali continues at this reduced rate with the computer 14 continuing to monitor the PH transducer 44.

When a PH of 8.2 is detected, the alkali shut-off valve 50 is closed to stop the titration. The stirrer is also stopped at 5B25 and the computer again interrogates the weight transducer 42 to determine and store the total weight of the titrated juice and the vessel 40. While acid content can be determined by titrating to another PH, a PH of 8.2 is conveniently chosen because it marks the beginning of a color break if a chemical indicator were used.

This completes the Brix-Acid test routine and the data obtained from this test is then used to compute the desired parameters and ratios which indicate the nature and quality of the fruit.

Figure 5C:
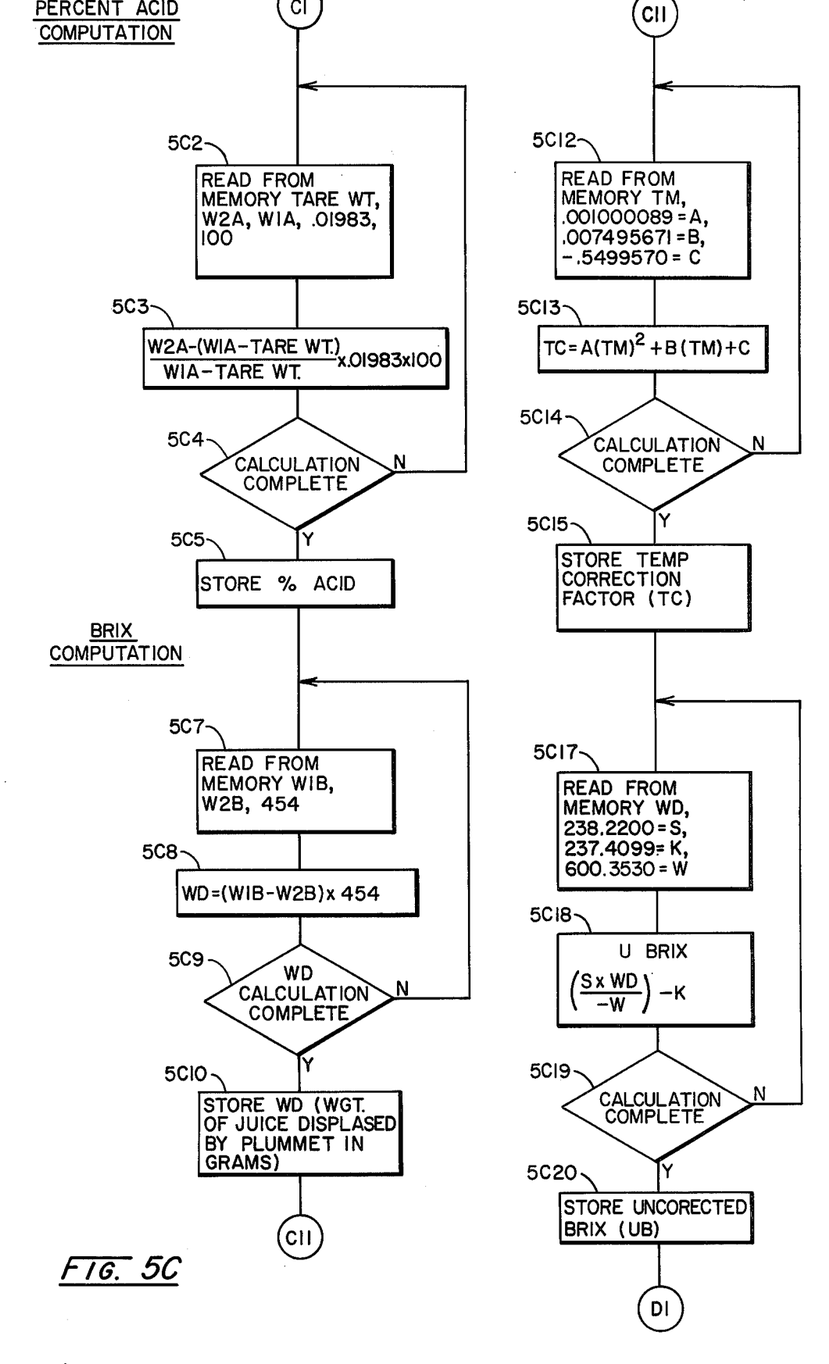

Referring to FIG. 5C, the per cent acid by weight may be computed according to the formula at 5C3 which is found in published literature. The formula indicates that the per cent acid is calculated by multiplying the fraction which consists of the weight of juice and alkali after titration less the weight of juice prior to titration divided by the weight of juice prior to titration times .01983 times 100. The fraction is of course the ratio of the weight of the alkali added during titration to the weight of the initial juice sample.

The operating sequence then continues at 5C7 by performing the Brix computations. First, the weight of the juice displaced by the plummet is found and converted to units of grams in steps 5C7-5C10. This is done according to the formula at 5C8 which is found in the published literature. The computer subtracts the weight of the plummet in juice from the weight of the plummet in air and multiplies the difference by 454 and then stores this weight in its memory.

The operating sequence then continues to 5C12 where a temperature correction factor is computed according to the formula at 5C13 which is also found in the published literature. This formula indicates that the temperature correction factor is equal to a constant, found at 5C12, times the square of the juice temperature plus a constant B, also found at 5C12, times the temperature of the juice plus a constant C also found at 5C12.

Beginning at 5C17, the operating sequence then computes the per cent of soluble solids in degrees Brix prior to any correction for temperature. This uncorrected Brix is found using the formula at 5C18. As shown in the published literature, a slope constant S is multiplied by the previously computed weight of juice displaced by the plummet and divided by a constant -W found at step 5C17 representing the weight of the plummet in water at 20° centigrade. From this is subtracted a unit correction factor K to provide an uncorrected percentage of soluble solids in degrees Brix. The factor K is experimentally determined and represents variations in testing unit 12 characteristics which may differ slightly from unit to unit.

Figure 5D:
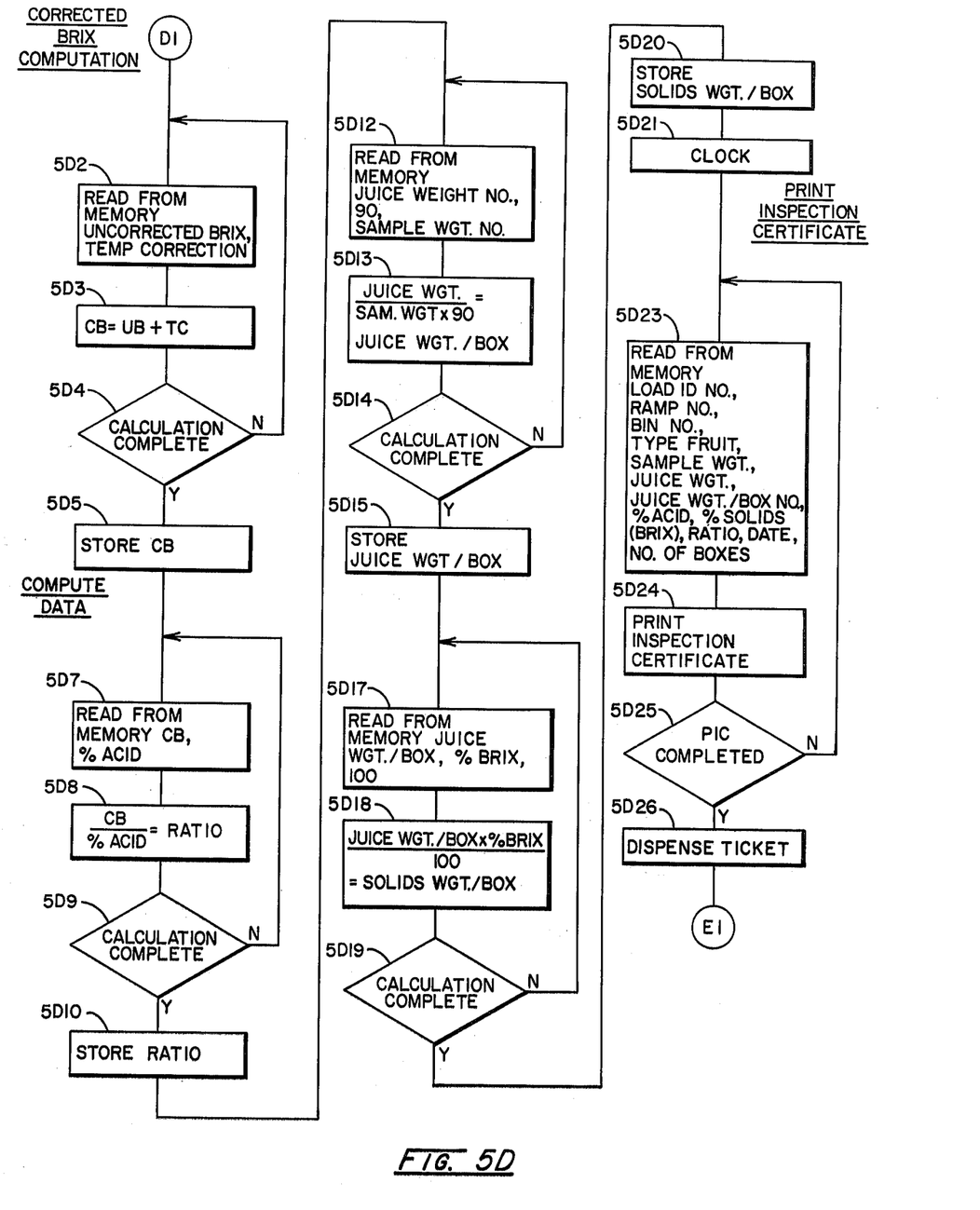

Referring to FIG. 5D, the actual, percentage by weight of soluble solids in the juice, or corrected Brix, may then be computed by adding the previously computed temperature correction factor to the previously computed uncorrected Brix according to the formula shown at step 5D3 and described in published literature. The corrected soluble solids content or corrected Brix is then stored in the computer memory.

The remainder of FIG. 5D illustrates, among other things, that a variety of other computations may be made using the percent acid and corrected Brix data previously computed.

For example, beginning at 5D8, the ratio of per cent soluble solids to per cent acid may be computed. Additionally it has been previously determined by citrus growing authorities that a standard box of citrus fruit weighs approximately 90 lbs. Consequently multiplication of 90 pounds by the ratio of juice weight to fruit weight, both of which were measured for a particular fruit sample and identified by a particular identification number, may be performed to determine the expected weight of juice in a box of fruit. This data is then stored at 5D15.

Because the units of degrees Brix represent the percentage of soluble solids by weight, the corrected Brix computation may be divided by 100 and multiplied by the juice weight per box as shown at 5D18 to yield the weight of soluble solids per box. This result is then stored as shown in step 5D20.

The computer may then print an inspection certificate upon which all of the entered and computed data may be printed as illustrated in the remainder of FIG. 5D. The operating sequence then branches to a rinse routine illustrated in FIG. 5E.

Figure 5E:
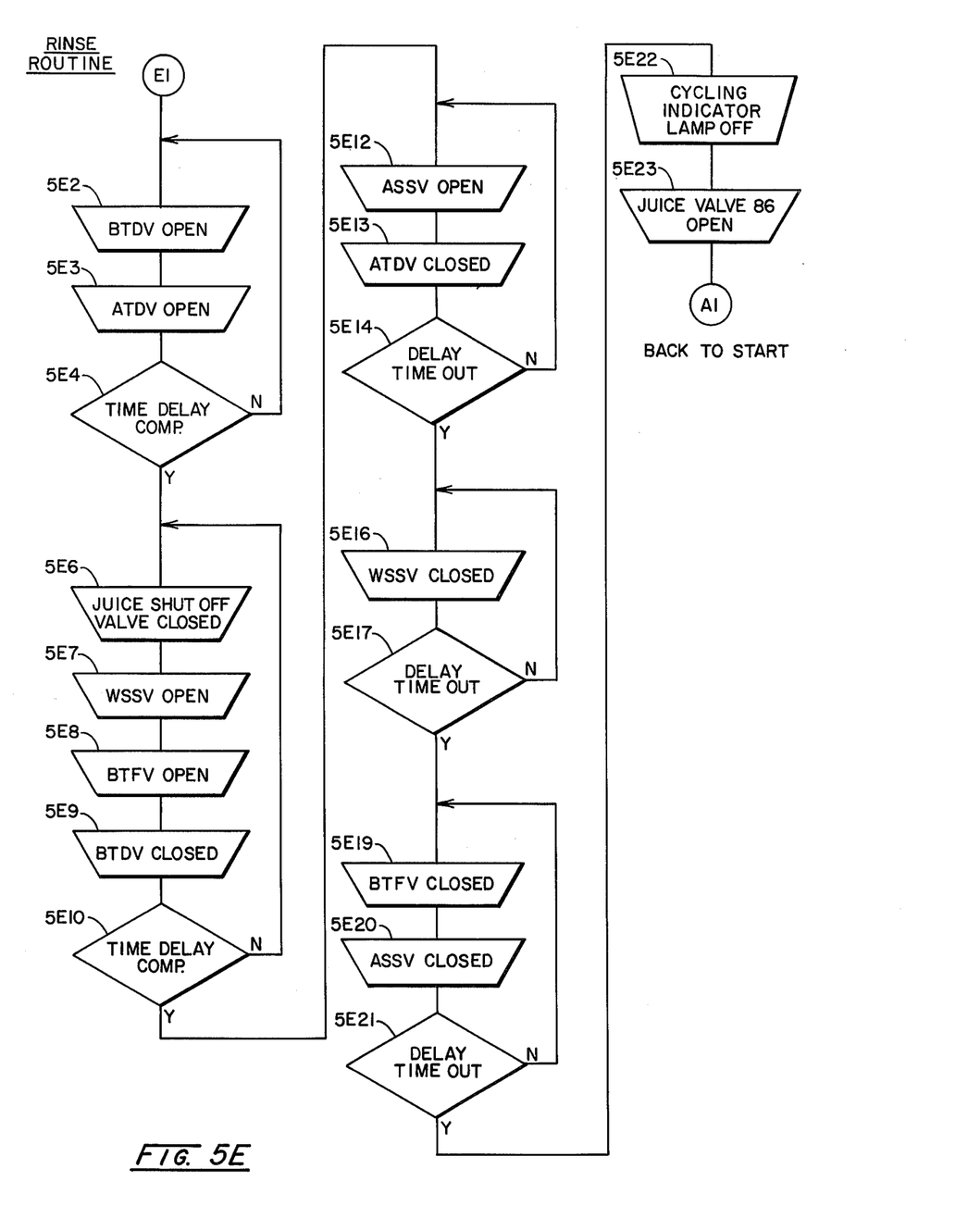

To initiate the rinse routine, the computer 14 opens the Brix test drain valve 62 and the acid test drain valve 68 for a selected period of time determined by a time-delay shown at step 5E4. The time delay is sufficiently long to permit the fruit juice samples to drain from the testing unit. The rinse water shut-off valve 84, and the Brix test fill valve are opened and the Brix test drain valve 62 is closed so that the Brix test vessel 30 may be filled with rinse water. After another similarly obtained time-delay, the acid sample shut-off valve 58 is opened and the acid test drain valve 68 is closed so that the acid test vessel 40 may similarly be filled with rinse water.

After a time delay which is sufficiently long to permit an overflow of rinse water, the rinse water shut-off valve 84 is closed. After another selected period of time delay which permits the sample filling conduit to drain, the Brix test fill valve 54 and the acid sample shut-off valve 58 are closed and a cycling indicator lamp is turned off to signal completion of the Brix-Acid testing unit 12 operation and that a new juice sample may be subsequently connected for testing.

The present invention therefore provides an automatic measurement of acid content and soluble solids content in a single unit. The test results are highly accurate because the testing unit does not attempt to control all the testing parameters but rather measures the existing parameters and then compensates or corrects the measured data for the existing parameters.

It is to be understood that while the detailed drawings and specific examples given describe preferred embodiments of the invention, they are for the purposes of illustration only, that the apparatus of the invention is not limited to the precise details and conditions disclosed and that various changes may be made therein without departing from the spirit of the invention which is defined by the following claims.

We claim:
1. A liquid analyzer for testing liquid comprising:
    (a) a soluble solids testing means for use in determining the soluble solids content of said liquid, said soluble solids testing means including a first vessel for receipt of a quantity of liquid, a plummet suspended in said first vessel from a first weight transducer, and a temperature transducer for detecting the temperature of said sample;
    (b) an acid testing means for use in determining the acid content of said liquid, said acid testing means including a second vessel for receipt of a quantity of liquid and supported by a second weight transducer, a PH transducer mounted to detect the PH of said sample, a stirrer for mixing the contents of said second vessel and an alkali source connected through an alkali inlet valve to deliver alkali to said second vessel;
    (c) a network of valved fluid conveying conduits interconnected with said soluble solids testing means and said acid testing means; and
    (d) controlling, computing and storage means associated with said soluble solids testing means, said acid testing means, and said fluid conveying conduits for automatically recording data representing the weight of said plummet suspended in said first vessel when empty, for loading liquid through said fluid conveying conduits into said vessels, for recording data representing the temperature of the liquid in said first vessel, the weight of the plummet in said liquid and the weight of the liquid in said second vessel, for actuating the stirrer, for opening the alkali inlet valve and delivering alkali into the quantity of liquid to titrate said quantity of liquid to a selected PH, for recording data representing the weight of the titrated second quantity of liquid in the second vessel, and for computing the acid and soluble solids content of said liquid.

2. An analyzer according to claim 1 further comprising a scale means connected to said controlling, computing and storage means for weighing and recording the weight of objects positioned thereon.

* * * * *